(12) United States Patent
Mathys et al.

(10) Patent No.: US 6,884,914 B2
(45) Date of Patent: Apr. 26, 2005

(54) OLEFIN OLIGOMERIZATION

(75) Inventors: Georges M. K. Mathys, Bierbeek (BE); Stephen H. Brown, Brussels (BE); Hubertus Joseph Beckers, Keerbergen (BE); Raphael Frans Caers, Edegem (BE); John Stephen Godsmark, Grez Doicheau (BE); Luc R. M. Martens, Meise (BE); John Richard Shutt, Tervuren (BE); Eddy T. Van Driessche, Eeklo (BE)

(73) Assignee: Exxon Mobil Chemical Patents Inc., Houston, TX (US)

( * ) Notice: Subject to any disclaimer, the term of this patent is extended or adjusted under 35 U.S.C. 154(b) by 432 days.

(21) Appl. No.: 10/061,822

(22) Filed: Feb. 1, 2002

(65) Prior Publication Data

US 2002/0111523 A1 Aug. 15, 2002

Related U.S. Application Data

(60) Provisional application No. 60/265,700, filed on Feb. 1, 2002.

(51) Int. Cl.$^7$ .............................................. C07C 2/207

(52) U.S. Cl. ...................... 585/324; 585/326; 585/327; 585/329; 585/518; 585/519; 585/639

(58) Field of Search ................................ 585/324, 326, 585/327, 329, 518, 519, 639

(56) References Cited

U.S. PATENT DOCUMENTS

| | | | | |
|---|---|---|---|---|
| 4,474,647 A | * | 10/1984 | Asselineau et al. | 203/49 |
| 4,579,999 A | * | 4/1986 | Gould et al. | 585/312 |
| 4,675,463 A | * | 6/1987 | Glivicky et al. | 585/514 |
| 4,929,780 A | | 5/1990 | Wright et al. | 585/303 |
| 5,026,933 A | * | 6/1991 | Blain et al. | 585/7 |

OTHER PUBLICATIONS

"Process for Upgrading C3, C4 and C5 Olefinic Streams," *Pet. & Coal*, vol. 37, No. 4 (1995).

* cited by examiner

Primary Examiner—Thuan D. Dang

(57) ABSTRACT

This invention is to a method of oligomerizing an olefin feed stream. The olefin feed stream contains at least one $C_2$ to $C_{12}$ olefin to obtain an olefin feed stream and has less than 1,000 ppm by weight oxygenated hydrocarbon. The olefin is oligomerized by contacting with an acid based oligomerization catalyst.

36 Claims, 1 Drawing Sheet

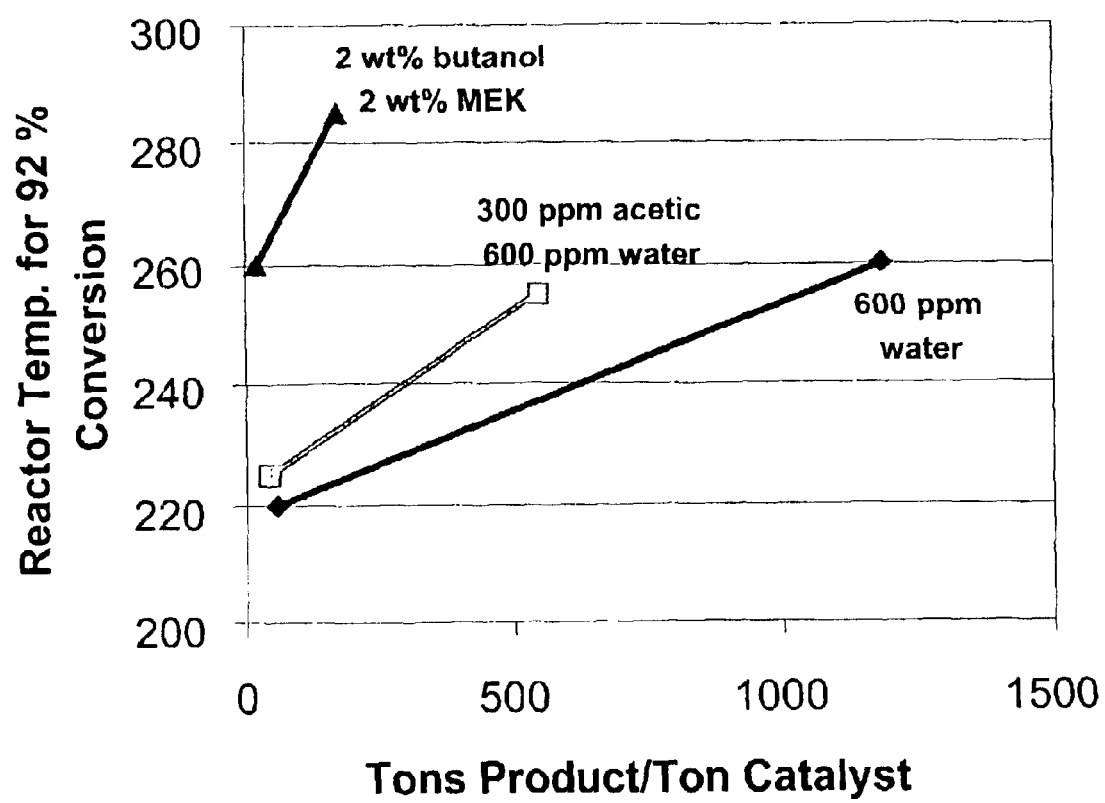

OLEFIN OLIGOMERIZATION

This application claims priority to U.S. Provisional Patent Application No. 60/265,700, filed Feb. 1, 2002.

FIELD OF THE INVENTION

This invention relates to a process for oligomerizing olefin. In particular, this invention relates to a process for oligomerizing an olefin stream containing a low concentration of oxygenated hydrocarbon contaminants.

BACKGROUND OF THE INVENTION

The oligomerization of olefin compounds is conventionally accomplished by catalytic reaction. Oligomerization catalysts are typically nickel based catalysts or acid based catalysts. Generally, oligomerization processes which use nickel based catalysts are carried out by forming a homogenous suspension of catalyst, olefin feed and product, whereas the acid based catalyst systems are carried out using a flow-through, fixed bed type of arrangement. The homogeneous suspension type of system is generally much more technically difficult to operate, but offers certain advantages in its ability to product a greater degree of "semi-linear" oligomer products. These semi-linear products are products with limited branches, and can be beneficial in certain uses such as further reaction to form plasticizers, solvents or diesel type fuels in which limited branching is desirable.

Cosyns, J. et al., in "Process for upgrading $C_3$, $C_4$ and $C_5$ olefinic streams," *Pet. & Coal*, Vol. 37, No. 4 (1995), describe a nickel based catalyst system known as the Dimersol® process. This process is useful for dimerizing or oligomerizing a variety of olefin feeds. In particular, the process is useful for dimerizing or oligomerizing propylene, butylene and pentylene streams.

U.S. Pat. No. 6,143,942, to Verrelst et al., describes the oligomerization of $C_2$ to $C_{12}$ olefins using a mixture of ZSM-5 and ZSM-22, and ZSM-57 and ZSM-22. The particular combination of catalysts produces a high yield of trimer products.

U.S. Pat. No. 5,874,661, to Verrelst et al., describes a system for reducing branching of oligomerized olefins. In this system, lower olefins, such as propene or butene, are oligomerized to an oligomer or higher olefin using an acid based catalyst such as ZSM-5. The higher olefin is then isomerized also using an acid based catalyst, such as ZSM-5 or ZSM-22, to isomerize the higher olefin and reduce the degree of branching. The isomerized higher olefin is then hydroformylated to form surfactants and polyolefin stabilizers.

U.S. Pat. No. 5,762,800, to Mathys et al., describes a process for oligomerizing $C_2$ to $C_{12}$ alkenes using a zeolite oligomerization catalyst. The catalytic life of the catalyst is increased by hydrating the olefin feed to the oligomerization reactor.

U.S. Pat. No. 6,049,017, to Vora et al., describes the dimerization of a predominantly n-butylene containing feed stream. The n-butylene feed stream is ultimately derived from an olefin stream containing a variety of butylenes produced by a methanol to olefins reaction unit. The butylene stream from the methanol to olefins unit is pretreated by a combination of partial hydrogenation of dienes and isobutylene removal by way of an MTBE process, before sending the resulting n-butylene stream to the dimerization unit.

Often, efficiency of the oligomerization process is reduced due to the presence of greater than desirable quantities of inert components in the feed stream; for example, alkanes such as propane and butane. These inert components, in essence, take a free ride through the reaction system, taking up valuable reactor volume without being reacted to desirable products. Therefore, multiple separations processes to remove inert components are often required.

Olefin feed streams can also contain contaminants that act as poisons to oligomerization catalysts. For example, nickel based oligomerization catalysts are quite sensitive to sulfur and nitrogen. Such contaminants can have a particularly significant impact on the active life of the catalyst, shortening the life of the catalyst to the point where the reaction process is not feasible to operate.

It is, therefore, desirable to provide olefin feed streams which can be oligomerized at high efficiency and run for an extended period without causing early replacement or regeneration of catalyst. It would be particularly desirable to take advantage of an olefin feed stream which needs little pretreatment for use in an oligomerization system.

SUMMARY OF THE INVENTION

This invention provides a method for oligomerizing an olefin feed without substantially adversely affecting catalyst life. The oligomer product can be obtained without having to treat the olefin feed to remove contaminants such as sulfur and nitrogen. The oligomer product is optionally converted to a hydroformylated product with desirable branching characteristics.

In one embodiment, the invention provides a method of oligomerizing olefin which comprises removing oxygenated hydrocarbon from an olefin stream containing at least one $C_2$ to $C_{12}$ olefin to obtain an olefin feed stream comprising less than 1,000 ppm by weight oxygenated hydrocarbon. The olefin feed is contacted with an acid based oligomerization catalyst to oligomerize the olefin in the olefin feed.

In another embodiment, the invention comprises contacting an oxygenate with a molecular sieve catalyst to form an olefin stream containing at least one $C_2$ to $C_{12}$ olefin. Oxygenated hydrocarbons showing up in the formed olefin stream are removed from the olefin stream to obtain an olefin feed stream comprising less than 1,000 ppm by weight oxygenated hydrocarbon. The olefin feed stream is then contacted with an acid based oligomerization catalyst to form an olefin oligomer.

An alternative embodiment comprises contacting the oxygenate with a molecular sieve catalyst to form an olefin stream containing at least one $C_2$ to $C_{12}$ olefin. The a $C_3$ to $C_6$ olefin stream is recovered from the olefin stream, and oxygenated hydrocarbon is removed from the olefin stream to obtain an olefin feed stream comprising less than 1,000 ppm by weight oxygenated hydrocarbon. The olefin feed stream is then contacted with an acid based oligomerization catalyst to form an olefin oligomer.

In another embodiment of the invention an olefin feed stream is provided which comprises at least one $C_2$ to $C_{12}$ olefin and oxygenated hydrocarbon. Preferably, the oxygenated hydrocarbon is provided in the olefin stream at a concentration of greater than 5 ppm by weight and less than 1,000 ppm by weight. The provided olefin stream is then contacted with a zeolite oligomerization catalyst to oligomerize the olefin in the olefin feed.

In yet another embodiment of the invention, the acid based oligomerization catalyst is a zeolite oligomerization catalyst. The zeolite oligomerization catalyst is desirably selected from the group consisting of TON, MTT, MFI, MEL, MTW, EUO, ZSM-57, ferrierites, offretites, ZSM-4, ZSM-18, Zeolite Beta, faujasites, zeolite L, mordenites, erionites and chabazites. Preferably, the zeolite oligomerization catalyst is ZSM-22, ZSM-23 or ZSM-57, more preferably the zeolite oligomerization catalyst is ZSM-22 or ZSM-23. The acid based oligomerization catalyst can also be a solid phosphoric acid catalyst.

Surface activated zeolites such as mono-dimensional 10-ring zeolites, such as ZSM-22 or ZSM-23, are also useful as oligomerization catalysts. Such selectivated catalysts produce near linear oligomers.

It is desirable to have a reasonable quantity of olefin in the olefin feed stream for better efficiency. Preferably, the olefin feed contains less than 50 wt % alkane; more preferably, the olefin feed contains at least 50 wt % olefin.

In another embodiment of the invention, catalyst life is prolonged by hydrating the olefin feed prior to contacting with the oligomerization catalyst, particularly a zeolite oligomerization catalyst. Preferably, the hydrated olefin feed has a water content of 0.05 to 2 weight percent.

BRIEF DESCRIPTION OF THE DRAWING

Examples of various embodiments of the invention are shown in the attached FIGURE which depicts data derived from the Examples.

DETAILED DESCRIPTION OF THE INVENTION

This invention provides a method of oligomerizing olefin by contacting an olefin feed with an acid based oligomerization catalyst. Examples of an acid based oligomerization catalyst include solid phosphoric acid catalysts and zeolite oligomeriation catalysts.

The solid phosphoric acid catalysts used in this invention can be any conventional solid phosphoric acid catalyst that is active in olefin oligomerization reactions. Such catalysts comprise phosphoric acid on a silicon based support. Examples include phosphoric acid on silica gel, diatomaceous earth, and kieselguhr. More specific examples are found in U.S. Pat. Nos. 2,586,852; 2,713,560; and 4,675,463, the descriptions of which are incorporated herein by reference.

The zeolite oligomerization catalysts can be any catalyst that is active in olefin oligomerization reactions. Such catalysts include, for example, zeolites of the TON structure type (for example, ZSM-22, ISI-1, Theta-1, Nu-10, KZ-2); zeolites of the MTT structure type (for example, ZSM-23, KZ-1); zeolites of the MFI structure type (for example, ZSM-5); zeolites of the MEL structure type (for example, ZSM-11); zeolites of the MTW structure type (for example, ZSM-12); zeolites with the EUO structure type (for example, EU-1); zeolite ZSM-57, or any member of the ferrierite structure family. Other examples of suitable catalysts are offretites, ZSM-4, ZSM-18 or zeolite beta. Synthesis of these catalysts are described in *Synthesis of High-Silica Aluminosilicate Zeolites* by P. A. Jacobs and J. A. Martens (published as volume 33 in the series *Studies in Surface Science and Catalysis*), the disclosure of which is incorporated herein by reference.

Additionally, the catalyst used in this invention can be a zeolite synthesized without addition of a template. Examples include faujasites, zeolite L, mordenites, erionites and chabazites, the structures of which are described in the *Atlas of Zeolite Structure Types* by W. M. Meier and D. H. Olson (published by Butterworths on behalf of the Structure Commission of the International Zeolite Association). Zeolite catalysts having crystal structures that are essentially the same as the crystal structures of the above-mentioned zeolite catalysts, but differ slightly therefrom in chemical composition, can also be used. Examples of such zeolites include zeolite catalysts obtained by removal of a number of aluminum ions from, or by steaming of, the above-mentioned zeolite catalysts, or zeolite catalysts obtained by addition of different elements, for example, by impregnation or cation exchange or by incorporation during the zeolite synthesis (for example boron, iron and gallium).

Zeolite oligomerization catalysts can be made by any suitable method. One conventional technique includes heating a reaction mixture containing a source of silicon oxide, a source of aluminum oxide and, if appropriate, an organic promoter, for example, a nitrogen or phosphorus-containing organic base, together optionally with an alkali metal base, and separating the porous aluminosilicate crystals (zeolite precursor crystals) formed. The precursor crystals are then calcined in air or oxygen at a temperature exceeding 500° C.; for example, at a temperature of 550° C. for about 10 to about 20 hours. In one embodiment, the calcined material is exchanged with ammonium ions ($NH_4+$) and subjected to conditions under which the ammonium ions decompose, with the formation of ammonia and a proton, thus producing an acidic form of the zeolite. Alternatively, the acidic form can be obtained by acid exchange with hydrochloric acid. If desired, however, the calcined material can be used as a catalyst without first being exchanged with ammonium ions, since the material then already possesses acidic sites. The activity of the material is then significantly lower than that of a material that has been exchanged with ammonium ions and then subjected to conditions under which the ammonium ions decompose.

Ammonium exchanged and calcined monodimensional 10-rings zeolites, examples of which include ZSM-22 and ZSM-23, can be treated to selectivate their surface, thereby forming a selectivated catlayst. This selectivation can be achieved in numerous ways. As one example, the zeolites can be titrated with an organic nitrogen base, such as collidine. See, for example, U.S. Pat. No. 5,026,933 to Blain et al., the description of which is incorporated herein by reference. Another example is by depositing a crystalline Si:Al layer on a core of zeolite, such as ZSM-22 or ZSM-23, where this layer has a higher Si:Al ratio than the untreated zeolite. See, for example, U.S. Pat. No. 6,013,851, the description of which is incorporated herein by reference.

The olefin feed stream that is to be oligomerized in this invention includes at least one $C_2$ to $C_{12}$ olefin. Preferably the olefin feed stream comprises at least one $C_2$ to $C_8$ olefin, more preferably at least one $C_3$ to $C_6$ olefin.

In one embodiment, the olefin feed steam that is oligomerized contains at least 50 wt % olefin. Preferably, the olefin feed stream comprises at least about 55 wt % olefin, more preferably at least about 60 wt % olefin.

In another embodiment, the olefin feed stream comprises less than about 50 wt % paraffin. More preferably, the olefin feed stream comprises less than about 45 wt % paraffin, more preferably less than about 40 wt % paraffin.

The inventors have found that the acid based oligomerization catalysts used in this invention are adversely sensitive to even low levels of oxygenated hydrocarbons in the olefin feed. This sensitivity is demonstrated by a significant reduction in catalyst life in the presence of certain levels of oxygenated hydrocarbons. The exhibited sensitivity is quite unexpected, since it is known that addition of low levels of water (a non-hydrocarbon oxygenate) to the olefin feed can actually increase the catalytic life of the zeolite oligomerization catalysts. See, for example, U.S. Pat. No. 5,672,800 which shows hydration can improve zeolite oligomerization catalyst life.

Examples of oxygenated hydrocarbon to which the acid based oligomerization catalysts are adversely sensitive are alcohols, aldehydes, ketones, ethers and carboxylic acids. Oxygenated hydrocarbons which particularly affect the acid based oligomerization catalysts include methanol, butyl alcohol, dimethyl ether, methyl ethyl ketone, acetic acid, and propionic acid.

In one embodiment of the invention, the olefin feed stream that is to be oligomerized comprises less than 1,000 ppm by weight of the oxygenated hydrocarbon. Preferably, the olefin feed stream that is to be oligomerized comprises less than about 900 ppm by weight of the oxygenated hydrocarbon, more preferably less than about 800 ppm by weight of the oxygenated hydrocarbon.

It is not necessary that the olefin feed stream be completely devoid of oxygenated hydrocarbon. An amount of oxygenated hydrocarbon can be present, so long as it does not significantly adversely affect catalytic life of the oligomerization catalyst. In this regard, an olefin feed stream containing greater than about 500 ppm by weight oxygenated hydrocarbon is tolerable. Preferably, the level is somewhat lower. A lower limit of greater than about 100 ppm by weight is more desirable, with a lower limit of at least about 50 ppm by weight being even more desirable, and a lower limit of at least about 5 ppm by weight being particularly preferred. Lower limits of oxygenated hydrocarbon are not warranted as the oligomerization catalyst can satisfactorily tolerate very low levels, and it is technically difficult to remove oxygenated hydrocarbons to lower levels; particularly when the olefin feed stream is derived from processes such as oxygenate to olefins processes, which will generally contain substantial quantities of oxygenated hydrocarbons in the olefin product.

In another embodiment of the invention, the olefin feed stream that is oligomerized in this invention is predominantly derived from an oxygenate to olefins unit; meaning that at least 50 wt % of the olefin feed, preferably at least 60 wt %, and more preferably at least 70 wt % of the olefin feed, is derived from an oxygenate to olefins unit. Such a feed stream should be low in sulfur, nitrogen and chlorine, to the extent that essentially no pretreatment will be required for removal of such components. In addition, such a feed stream should have a relatively low concentration of paraffins, compared to such sources as olefins from cracked hydrocarbon source. However, such a feed stream will generally contain oxygenated hydrocarbon at a level which would likely adversely impact catalytic life of the zeolite oligomerization catalyst. Therefore, removal of such components are likely required. The benefit in using an oxygenate to olefins stream is that lower levels of inert components, such as propane and butane, are present.

Desirably, the olefin feed stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

A molecular sieve catalyst is used in this invention in the oxygenate to olefin reaction. Such a molecular sieve is defined as any molecular sieve capable of converting an oxygenate to an olefin compound. Examples of these molecular sieves include zeolites as well as non-zeolites, and are of the large, medium or small pore type. Small pore molecular sieves are preferred in one embodiment of this invention, however. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Zeolites which are particularly useful as an oxygenate to olefins catalyst include the ZSM type zeolites. Examples of the ZSM type zeolites include ZSM-4, ZSM-5, ZSM-11, ZSM-12, ZSM-13, ZSM-22, ZSM-23, and ZSM-57.

Another type of olefin forming catalyst useful in this invention is one containing a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the oxygenate to olefins catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46. The ALPOs can also include a metal substituent in its framework. Preferably, the metal is selected from the group consisting of magnesium, manganese, zinc, cobalt, and mixtures thereof. These materials preferably exhibit adsorption, ionexchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-1 1, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 microns to about 3,000 microns, more preferably from about 30 microns to about 200 microns, most preferably from about 50 microns to about 150 microns.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A preferred catalyst of this invention is a catalyst which contains a combination of SAPO-34, and SAPO-18 or ALPO-18 molecular sieve. In a particularly preferred embodiment, the molecular sieve is a crystalline intergrowth of SAPO-34, and SAPO-18 or ALPO-18.

To convert oxygenate to olefin for use as olefin feed, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The oxygenate to olefins process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

Olefins obtained by cracking hydrocarbon streams can also be used to form the olefin feed stream of this invention. It is preferable, however, that such olefins be combined with the olefin product of the oxygenate conversion reaction. This is because the olefins obtained by a cracking process are generally high in non-reactive hydrocarbon components such as alkanes, are high in branchiness, and are high in other undesirable by-products such as sulfur, which can cause conversion problems in the higher olefin reaction process. Therefore, additional purification of such a stream would be needed.

The olefin feed of this invention has a substantially reduced sulfur, nitrogen and/or chlorine content. According to one embodiment, the olefin feed also contains isoolefin at a concentration that does not substantially adversely affect the linear quality of dimerized or oligomerized product. Such product contains enough n-olefin and mono-branched mono-olefin to provide derivative products, particularly esters, that are highly desirable for industrial end uses. Ester derivatives from the dimer and oligomer products of this invention will be particularly suitable for use as plasticizers.

The sulfur content of the olefin feed of this invention should be sufficiently low such that the activity of the catalyst used to form the olefin dimer or oligomer is not substantially inhibited. Preferably, the sulfur content in the olefin feed is not greater than about 1 ppm; more preferably, not greater than about 0.5 ppm; and most preferably, not greater than about 0.3 ppm by weight, calculated on an atomic basis.

The nitrogen content of the olefin feed of this invention should also be sufficiently low such that the catalytic activity of the catalyst used to form the olefin dimer or oligomer is not substantially inhibited. Preferably, the nitrogen content in the olefin feed is not greater than about 1 ppm; more preferably, not greater than about 0.5 ppm; and most preferably, not greater than about 0.3 ppm by weight, calculated on an atomic basis.

The chlorine content of the olefin feed of this invention should also be sufficiently low such that the catalytic activity of the catalyst used to form the olefin dimer or oligomer is not substantially inhibited. Preferably, the chlorine content in the olefin feed is not greater than about 0.5 ppm; more preferably, not greater than about 0.4 ppm; and most preferably, not greater than about 0.3 ppm by weight, calculated on an atomic basis.

It is also desirable, according to one embodiment, that the olefin feed stream of this invention be high in linear mono-olefin content so as to maintain a sufficiently high conversion to higher olefin product having few branches. Preferably, the olefin feed stream comprises at least about 50 wt % linear monoolefin, more preferably at least about 60 wt % linear mono-olefin; and most preferably at least about 70 wt % linear mono-olefin. Preferably, the linear monoolefin is a $C_2$ to $C_6$ linear mono-olefin and has a $C_6$ and higher hydrocarbon content of not greater than about 20 wt %; more preferably, not greater than about 15 wt %; and most preferably, not greater than about 10 wt %.

The olefin feed streams of this invention are contacted with the acid based oligomerization catalyst in order to form desirable dimer and/or oligomer products. As used herein, dimerization and oligomerization processes are considered interchangeable terms. The processes are also known as higher olefins processes. Dimerization processes, oligomerization processes and higher olefins forming processes are all phrases that define the dimerization and/or oligomerization of light olefins, particularly $C_3$–$C_6$ olefins, to form a dimer or oligomer product, the product also referred to as a higher olefin.

Conventional processes for removing oxygenated hydrocarbons from olefin streams can be used to produce the olefin feed stream used in this invention. Such methods include water and alcohol washing, caustic scrubbing, distillation, extractive distillation and fixed bed adsorption. Other desirable methods, such as those found in *Kirk-Othmer Encyclopedia of Chemical Technology*, 4th edition, Volume 9, John Wiley & Sons, 1996, pg. 894–899, the description of which is incorporated herein by reference, can also be used. In addition, purification systems such as that found in *Kirk-Othmer Encyclopedia of Chemical Technology*, 4th edition, Volume 20, John Wiley & Sons, 1996, pg. 249–271, the description of which is also incorporated herein by reference, can be used.

In one embodiment of the invention, olefin feed streams that are oligomerized according to this invention can be derived from a main olefin source and treated to reduce oxygenated hydrocarbon content. The treated olefin stream can then be further separated to produce an olefin feed of a particularly preferred range, e.g., $C_2$ to $C_6$ olefins.

In another embodiment of the invention, the olefin feed stream that is to be oligomerized is separated according to a particularly preferred range, and the separated olefin feed is treated to reduce oxygenated hydrocarbon. The order of separation and/or treatment to reduce oxygenated hydrocarbon content is not critical to the invention.

In another embodiment of the invention, acid based oligomerization catalyst life, particularly the life of zeolite oligomerization catalysts are increased by hydrating the olefin feed stream prior to contacting the stream with the catalyst. This means that an amount of water effective in substantially increasing catalyst life is added. Preferably, water is added to the olefin feed stream such that the stream comprises from about 0.05 weight percent to about 2 weight percent water. More preferably, water is added to the olefin feed stream such that the stream comprises from about 0.1 weight percent to about 1 weight percent water. The desired proportion of water may be incorporated by saturating the feed at an appropriate temperature, e.g., from about 25° C. to about 60° C., or by injecting water through a pump.

The oligomerization reaction process can take place at any temperature effective in oligomerizing olefin feed to oligomer product. In general, the reaction takes place at a temperature of from about 170° C. to about 300° C., preferably from about 170° C. to about 260° C., and most preferably from about 180° C. to about 260° C.

Operating pressures are not critical to the oligomerization reaction. In general the reaction process is carried out at a pressure of from about 5 MPa to about 10 MPa, preferably from about 6 MPa to about 8 MPa.

Flow of olefin feed through the reactor should be sufficient to carry out a reasonably high conversion, but not so low that there are significant amounts of undesirable side reactions. In general, the reaction is carried out at a weight hourly space velocity (WHSV) of from about 0.1 $hr^{-1}$ to about 20 $hr^{-1}$, preferably from about 1 $hr^{-1}$ to about 10 $hr^{-1}$, and most preferably from about 1.5 $hr^{-1}$ to about 7.5 $hr^{-1}$.

Following the oligomerization reaction, the higher olefin product is optionally recovered, and further converted to desirable derivative products. These derivative products can be paraffin mixtures, obtained by conventional hydrogenation processes and optional blending and/or additional distillation. The paraffin mixtures can be used as hydrocarbon fluids and/or solvents in many applications, including paints and coatings, process fluids, metal cleaning, dry cleaning, cosmetics, pharmaceuticals, agrochemicals, degreasing, aerosol propellants, adhesives, cleaners, inks, and other industrial and household products.

Other higher olefins derivatives include thiols (often called mercaptans) or sulfides, which are produced by reacting with a sulfur compound. These are valuable starting materials for agricultural chemicals, pharmaceuticals, cosmetic ingredients, antioxidants, fragrance components and polysulfides. They are also used as polymerization regulators in rubber and plastics manufacture.

Examples of other derivatives include alkylated aromatics, using conventional alkylation processes. The alkylated aromatics can be further processed to their lubricant components or surfactant derivatives, or used as a hydrocarbon fluid as is.

A particularly desirable conversion process for higher olefins is carbonylation in general or hydroformylation in particular. These processes lead to various derivatives, including esters, aldehydes, and alcohols. An overview of catalysts and reaction conditions of hydroformylation processes is given for example by Beller et al. in *Journal of Molecular Catalysis*, A104 (1995), pages 17–85, the details of which are incorporated herein by reference. See also *Ullmanns Encyclopedia of Industrial Chemistry*, Vol. A5 (1986), pages 217 to 233; which is also incorporated herein by reference. Further description is found in J.Falbe, *Carbon Monoxide in Organic Synthesis*, 1967; and J.Falbe, *New Synthesis with Carbon Monoxide*, 1980.

Hydroformylation involves the contacting of the higher olefin product, carbon monoxide and hydrogen with the hydroformylation catalyst or its precursor. Hydroformylation catalysts are organometallic complexes of the metals of Group VIII of the periodic system, optionally used in combination as bi or tri-metallic systems, and optionally with salts of other metals as promoters, for example tin chloride. The catalytic organometallic complexes are combinations of catalytic metals with various ligands. Preferred metals are cobalt, rhodium and palladium.

The organometallic catalyst can be introduced as the active organometallic complex, or the complexes can be made in situ from catalyst precursors and ligands introduced into a reaction zone. Suitable catalyst precursors include, for example, the respective metal hydrides, halides, nitrates, sulfates, oxides, sulfides and salts of organic acids. Such acids include formates, acetates, or heavier alkylcarboxylic acids such as oleates or naphthenates. Other organic acids which can be used include alkylsulfonic or arylsulfonic acids.

Particularly desirable complexes for the hydroformylation of the higher olefins of this invention are the carbonyl compounds of the metals mentioned, as well as those containing amines, triorganic derivatives of phosphorous, arsenic or antimony, the respective oxides of these derivatives, optionally functionalized to make them soluble in phases that under certain conditions can be separated from the organic reactor liquid.

Hydroformylation is desirably carried out at a temperature ranging from about 40° C. to about 220° C. Preferred is a temperature ranging from about 80° C. to about 200° C.; particularly about 90° C. to about 180° C.

Hydroformylation can be carried out at conventional hydroformylation pressure ranges. In general, hydroformylation is acceptable at a pressure range of from about 1 to about 400 bar gauge. Medium and high pressure ranges are preferred ranges. In general, medium and high pressure ranges are considered to be in the range of about 40 to about 400 bar gauge, more specifically in the range of about 50 to about 320 bar gauge. Within these general pressure ranges CO-liganded catalyst processes are particularly useful.

A high pressure range is generally considered in the range of about 175 to about 400 bar gauge, more desirably about 190 to about 310 bar gauge. CO-liganged rhodium and cobalt catalyst processes are particularly useful in these high pressure ranges.

A medium pressure range is generally considered to be in the range of about 40 to about 175 bar gauge, more desirably about 50 to about 150 bar gauge, and with certain catalysts it is desirable to be within a range of from about 60 to about 90 bar gauge. As an example, a triphenylphosphineoxide (TPPO)-liganded rhodium catalyst is particularly desirable in the range of from about 50 to about 150 bar guage. As another example, a trialkylphosphine-liganded cobalt catalyst is particularly desirable in the range of from about 60 to about 90 bar gauge.

Hydroformylation can also be carried out in low pressure ranges. In general, the low pressure range will be in the range of from about 5 to about 50 bar gauge, although a pressure range of from about 10 to about 30 bar gauge is particularly useful. An example of a hydroformylation catalyst which is particularly useful in the low pressure range is phosphine-liganded rhodium, more particularly triphenylphosphine-liganded rhodium.

Other hydroformylation catalysts can be used within the pressure ranges described. Such catalysts are described in *Kirk-Othmer*, $4^{th}$ Edition, Volume 17, "Oxo Process," pages 902–919 and *Ullman's Encyclopedia of Industrial Chemistry*, $5^{th}$ Edition, Volume A18, "Oxo Synthesis," pages 321–327, the detailed descriptions of each being incorporated herein by reference.

It is desirable in some instances that hydroformylation be carried out at a carbon monoxide partial pressure not greater than about 50% of the total pressure. The proportions of carbon monoxide and hydrogen used in the hydroformylation or oxo reactor at the foregoing pressures are desirably maintained as follows: CO from about 1 to about 50 mol %, preferably from about 1 to about 35 mol %; and $H_2$ from about 1 to about 98 mol %, preferably from about 10 to about 90 mol %.

The hydroformylation reaction is conducted in a batch mode according to one embodiment. Alternatively, the hydroformylation reaction can occur on a continuous basis. In a continuous mode, a residence time of up to 4 hours is useful. If a plurality of reactors is employed, a residence time as short as 1 minute is advantageous. Alternatively a residence time is in the range of from about ½ to about 2 hours is useful.

Since the hydroformylation process of the invention takes place in the liquid phase and the reactants are gaseous compounds, a high contact surface area between the gas and liquid phases is desirable to avoid mass transfer limitations. A high contact surface area between the catalyst solution and the gas phase is obtainable in a variety of ways. For example and without limitation, contact surface area between the gaseous reactants and the liquid phase is obtained by stirring in a batch autoclave operation. In a continuous operation, the olefin feed stream of one embodiment is contacted with catalyst solution in, for example, a continuous-flow stirred autoclave where the feed is introduced and dispersed at the bottom of the vessel, preferably through a perforated inlet. Good contact between the catalyst and the gas feed is obtainable by dispersing a solution of the catalyst on a high surface area support. Such a technique is commonly referred to as supported liquid phase catalysis. The catalyst is provided as part of a permeable gel.

The hydroformylation reaction is performed in a single reactor according to one embodiment. Examples of suitable reactors are found in U.S. Pat. Nos. 4,287,369 and 4,287,370 (Davy/UCC); U.S. Pat. No. 4,322,564 (Mitsubishi); U.S. Pat. No. 4,479,012 and EP-A-114,611 (both BASF); EP-A-103,810 and EP-A-144,745 (both Hoechst/Ruhrchemie); and U.S. Pat. No. 5,763,678 (Exxon). Two or more reactor vessels or reactor schemes configured in parallel are used in another embodiment. In addition, a plug flow reactor design, optionally with partial liquid product backmixing, provides an efficient use of reactor volume.

It is preferred, according to one embodiment, that the hydroformylation reaction be carried out in more than one reaction zone or vessel in series. Suitable reactor configurations are disclosed, for example, by Fowler et al in British Patent Specification No. 1,387,657, by Bunning et al in U.S. Pat. No. 4,593,127, by Miyazawa et al in U.S. Pat. No. 5,105,018, by Unruh et al in U.S. Pat. No. 5,367,106. and by Beckers et al. in U.S. Pat. No. 5,763,678. Examples of individual hydroformylation reactors can of the standard types described by Denbigh and Turner in *Chemical Reactor Theory* ISBN 0 521 07971 3, by Perry et al in *Chemical Engineers' Handbook* ISBN 0-07-085547-1 or any more recent editions, e.g., a continuous stirred tank or a plug flow reactor with adequate contact of the gas and the liquid flowing through the reactor. Advantageously these plug flow reactor designs or configurations include ways of partial backmixing of the reactor product liquid, as explained, for example, by Elliehausen et al in EP-A-3,985 and in DE 3,220,858.

Hydroformylated products have utility as intermediates in the manufacture of numerous commercially important chemicals, with the invention further providing processes in which hydroformylation is followed by reactions producing such chemicals. The reaction products will typically be a mixture of oxygenated compounds, since the higher olefin components used to make the products will generally include a mixture of components. The higher olefin components are generally a mixture of components, because the olefin feed stream that is used to make the oligomeric olefin product will generally include a mixture of olefins. However, the resulting hydroformylation product stream will generally be higher in linearity as a result of the high degree of linearity of the oligomeric olefin and olefin compositions used upstream of the hydroformylation reaction process.

Either in their pure form, or as part of the mixture in the hydroformylation product, aldehydes which are produced are optionally aldolized, a term which includes the dehydration of the aldol condensate to form an unsaturated aldehyde. This aldolization can be performed with the other aldehydes present in the stream, or with aldehydes that were prepared separately and are added to the original aldehyde or hydroformylation product stream.

Aldol product is optionally hydrogenated to the corresponding alcohol mixture. If desired, the unsaturated aldehyde mixture from aldolization can be selectively hydrogenated to form the saturated aldehyde mixture. Any of the saturated aldehyde mixtures, either as made by hydroformylation or by selective hydrogenation of an aldol product, can have special value when they are oxidized to their corresponding carboxylic acids, or condensed with formaldehyde to polyols, or with ammonia to imines which can be hydrogenated to amines. The acids and polyols are valuable intermediates for esters, polyol esters, metal salts, amides, and again for imines and amines.

Under circumstances where the olefin feed is ultimately derived from a low-value feedstock like natural gas, i.e., in cases where methane from natural gas is converted to methanol and the methanol to olefin, the products or product mixtures may have value as liquid transportable fuels, optionally after dehydration to the olefin, and if desired hydrogenation to a paraffin or paraffinic mixture. Particularly valuable compositions produce according to this invention are isononyl alcohol mixtures, made by hydroformylation and hydrogenation of octene mixtures. The invention also provides a valuable process for the manufacture of isooctanoic acid, wherein the aldehyde from hydroformylation of a heptene mixture is separated from the hydroformylation product and subsequently oxidized.

In another embodiment of the invention, the hydroformylation products of this invention are optionally hydrogenated to saturated alcohols. Formation of a saturated alcohol may be carried out, if desired, in two stages through a saturated aldehyde, or in a single stage to the saturated alcohol, in which case it is desirable to form a saturated aldehyde as an intermediate. The alcohols are then optionally esterified, etherified, or formed into acetals or carbonates, which can be used as plasticizers, surfactants or synthetic lubricants. The esters and ethers of the invention, or produced by the process of the invention, are suitable for use as solvents, paint coalescers, plasticizers, adhesives, surfactants, viscosity index improvers, synthetic lubricants, flame retardants, lubricant components, anti-wear agents, hydraulic fluids, cetane improvers, drilling fluids, thermoplastic and textile processing aids, polymer, especially vinyl chloride polymer, stabilizers, polymerizable monomers and fragrances.

Esterification is accomplished by reacting the alcohols of this invention with acids or anhydrides. The reaction process desirably takes advantage of conventional processes. In these conventional processes, it is desirable to react the alcohols and acids at elevated temperatures and pressures, and to drive the reaction toward completion by removing water that is produced as a by-product.

Catalysts may be employed in the esterification reaction. Suitable catalysts include, for example, titanium containing catalysts, e.g., a tetraalkyl titanate, in particular tetra-isopropyl or tetraoctyl ortho titanate, or sulphonic acid containing catalysts, e.g., p-toluene sulphonic acid or methylsulphonic acid. Also sulphuric acid catalyst may be used. Alternatively, the esterification reaction may be preformed without the addition of a dedicated catalyst.

Catalyst present in the esterification reaction product may be removed by alkali treatment and water washing. Advantageously, the alcohol is used in slight, e.g., from 10 to 25%, molar excess relative to the number of acid groups in the acid.

The acid of the ester may be inorganic or organic; if the latter, a carboxylic acid is preferred. Aromatic acids or their anhydrides are preferred for plasticizer manufacture, although aliphatic acids are also employed. Additional examples of acids include, acetic, propionic, valeric, isovaleric, n-heptanoic, noctanoic, n-decanoic, neodecanoic, lauric, stearic, iso-stearic, oleic, erucic, succinic, phthalic (1,2-benzenedicarboxylic), isophthalic, terephthalic, adipic, fumaric, azelaic, 2-methylpentanoic, 2,4-dimethylheptanoic, 2,4,6-trimethylnonanoic, sebacic, benzoic, trimellitic, pyromellitic, acrylic, methacrylic, tall oil, monobasic or dibasic cyclohexanoic, naphthenic and naphthalene-type acids, carbonic, nitric, sulphuric, phosphoric and phosphorous and their thioanalogous, acids and $C_6$ to $C_{13}$ oxo and neo acids. The esters of the $C_9$ and especially the $C_{12}$ alcohols with oxo and neo acids are especially useful as drilling fluids and power transmission fluids. Phosphate esters are particularly desirable as flame retardants; while phosphite esters provide vinyl chloride polymer stabilizers.

Esters with monobasic and dibasic acids are preferred for lubricants and lubricant components. Advantageously the resulting esters contain from 15 to 40 carbon atoms. Adipates, azelates, and phthalates are especially preferred for lubricant manufacture. Esters with unsaturated carboxylic acids, e.g., with acrylic and methacrylic acid, provide polymerizable monomers, suitable as sole or comonomer in thermoplastics manufacture, or in polymers used in or as adhesives, VI improvers, and coating resins.

The esters of the invention may be used as a plasticizer for numerous polymers. Examples include cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated carboxylic acids e.g., methacrylates, and/or olefins; nitrile rubbers; and postchlorinated vinyl chloride polymers. Poly(vinyl chloride) is of particular interest.

The proportion of plasticizer ester to polymer may vary within wide limits. A desirable range is from about 10 to about 200 parts by weight per 100 parts of polymer, preferably from about 20 to about 100 parts per 100 parts of polymer.

The esters of the invention may be used alone as plasticizer, or in admixture with one another, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, or butyl benzyl phthalate, or mixtures thereof. They may also, or instead, be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. For example, they may be in the form of a dryblend, a paste, or a plastisol, depending on the grade of the resin employed. They may be used, for example, as coatings, in dipping, spraying, injection or rotational molding, extrusion, or as self-supporting films and sheets, and may readily be foamed. End uses include flooring materials, wall coverings, molded products, upholstery materials, leather substitutes, electrical insulation, especially wire and cable, coated fabrics, toys, and automobile parts.

The invention also provides a composition comprising an ester of the invention and a refrigerant, especially a fluorocarbon refrigerant, and more especially HFC 32 (difluoromethane) or HFC 134a (1,1,1,2-tetrafluoroethane). More especially, the invention provides such a composition also comprising at least one of a hydrolytic stability enhancer, e.g., a hindered phenol or an aromatic amine, an antioxidant, corrosion inhibitor, and a metal deactivator.

The following examples represent various embodiments of the invention, within the overall scope of the invention as described in the claims.

EXAMPLE 1

An olefin feed comprising 64 wt % butenes and 35 wt % butane, the balance comprising propane and propylene was hydrated by passing the olefin feed at a temperature of about 39° C. through a thermostated water saturator prior to introducing the feed into an oligomeriztion reactor containing ZSM-22. The hydrated feed, which contained 600 ppm by weight water, was then contacted with the ZSM-22 in the reactor to determine catalyst life at 92% conversion. The results are shown in the FIGURE.

EXAMPLE 2

Acetic acid was added to a portion of the hydrated olefin feed in Example 1 to obtain an acetic acid concentration of 300 ppm by weight. The olefin feed was then contacted with ZSM-22 catalyst in an oligomerization reactor to determine catalyst life at 92% conversion. The results are shown in the FIGURE.

EXAMPLE 3

Butanol and methyl ethyl ketone (MEK) was added to an olefin feed comprising 64 wt % butenes and 35 wt % butane, the balance comprising propane and propylene to obtain an olefin feed stream containing 2 wt % butanol and 2 wt % MEK. The resulting olefin feed stream was then contacted with ZSM-22 in an oligomerization reactor to determine catalyst life at 92% conversion. The results are shown in the FIGURE.

The data of Examples 1–3, as shown in the FIGURE, demonstrate that oxygenated hydrocarbon can adversely affect catalyst life of zeolite oligomerization catalyst.

Having now fully described this invention, it will be appreciated by those skilled in the art that the invention can be performed within a wide range of parameters within what is claimed, without departing from the spirit and scope of the invention.

What is claimed is:

1. A method of making an olefin oligomer from an oxygenate, comprising:
    contacting the oxygenate with a molecular sieve catalyst to form an olefin stream containing at least one $C_2$ to $C_{12}$ olefin;
    removing oxygenated hydrocarbon from the olefin stream to obtain an olefin feed stream comprising less than 1,000 ppm by weight oxygenated hydrocarbon; and
    contacting the olefin feed stream with an acid based oligomerization catalyst an olefin oligomer, wherein the olefin feed stream is hydrated prior to contacting with the oligomerization catalyst.

2. The method of claim 1, wherein the acid based oligomerization catalyst is a solid phosphoric acid catalyst.

3. The method of claim 1, wherein the acid based oligomerization catalyst is a zeolite oligomerization catalyst.

4. The method of claim 3, wherein the zeolite oligomerization catalyst is selected from group consisting of TON, MTT, MFI, MEL, MTW, EUO, ZSM-57, ferrierites, offretites, ZSM-4, ZSM-18, ZSM-23, Zeolite Beta, faujasites, zeolite L, mordenites, erionites and chabazites.

5. The method of claim 4, wherein the zeolite oligomerization catalyst is ZSM-22, ZSM-23 or ZSM-57.

6. The method of claim 5, wherein the zeolite oligomerization catalyst is ZSM-22 or ZSM-23.

7. The method of claim 6, wherein the zeolite oligomerization catalyst is a selectivated catalyst.

8. The method of claim 1, wherein the olefin feed contains less than 50 wt % alkane.

9. The method of claim 8, wherein the olefin feed contains at least 50 wt % olefin.

10. The method of claim 1, wherein the oxygenate is methanol or dimethyl ether.

11. The method of claim 1, wherein the hydrated olefin feed has a water content of 0.05 to 2 weight percent.

12. The method of claim 1, wherein the olefin feed stream comprises greater than 5 ppm by weight oxygenated hydrocarbon.

13. The method of claim 12, wherein the olefin feed contains less than 50 wt % alkane.

14. The method of claim 13, wherein the olefin feed contains at least 50 wt % olefin.

15. A method of making an olefin oligomer from an oxygenate, comprising:
a) contacting the oxygenate with a molecular sieve catalyst to form an olefin stream
b) recovering an olefin stream containing at least one $C_3$ to $C_6$ olefin from the olefin stream of step a),
c) removing oxygenated hydrocarbon from the olefin stream of step b) to obtain an olefin feed stream comprising less than 1,000 ppm by weight oxygenated hydrocarbon; and
d) contacting the olefin feed stream of step c) with an acid based oligomerization catalyst to form an olefin oligomer, wherein the olefin feed stream is hydrated prior to contacting wit the oligomerization catalyst.

16. The method of claim 15, wherein the acid based oligomerization catalyst is a solid phosphoric acid catalyst.

17. The method of claim 15, wherein the acid based oligomerization catalyst is a zeolite oligomerization catalyst.

18. The method of claim 17, wherein the zeolite oligomerization catalyst is selected from the group consisting of TON, MTT, MFI, MEL, MTW, EUO, ZSM-57, ferrierites, offretites, ZSM-4, ZSM-18, ZSM-23, Zeolite Beta, faujasites. zeolite L, mordenites, erionites and chabazites.

19. The method of claim 18, wherein the zeolite oligomerization catalyst is ZSM-22, ZSM-23 or ZSM-57.

20. The method of claim 19, wherein the zeolite oligomerization catalyst is ZSM-22 or ZSM-23.

21. The method of claim 20, wherein the zeolite oligomerization catalyst is selectivated cat.

22. method of claim 15, wherein the oxygenate is dimethyl ether.

23. The method of claim 15, wherein the hydrated olefin feed has a water content of 0.05 to 2 weight percent.

24. The method of claim 15, wherein the olefin feed stream comprises greater than 5 ppm by weight oxygenated hydrocarbon.

25. A method of making an olefin oligomer from an oxygenate, comprising:
a) contacting the oxygenate with a molecular sieve catalyst to form an olefin stream;
b) removing oxygenated hydrocarbon from the olefin stream of step a);
c) recovering an olefin stream containing at least one $C_3$ to $C_6$ olefin from the olefin stream of step b), following removal of the oxygenated hydrocarbon, to obtain an olefin feed stream, wherein the olefin feed stream contains less than 1,000 ppm by weight oxygenated hydrocarbon; and
d) contacting the olefin feed with an acid based oligomerization catalyst to form an olefin oligomer, wherein the olefin feed stream is hydrated prior to contacting with the oligmerization catalyst.

26. The method claim 25, wherein the acid based oligomerization catalyst is a solid phosphoric acid catalyst.

27. The method of claim 25, wherein the acid based oligomerization catalyst is a zeolite oligomerization catalyst.

28. The method of claim 27, wherein the zeolite oligomerization catalyst is selected from the group consisting of TON, MTT, MFI, MEL, MTW, EUO, ZSM-57, ferrierites, offretites, ZSM-4, ZSM-18, ZSM-23, Zeolite Beta, faujasites, zeolite L, mordenites. erionites and chabazites.

29. The method of claim 28, wherein the zeolite oligomerization catalyst is ZSM-22, ZSM-23 or ZSM-57.

30. The method of claim 29, wherein the zeolite oligomerization catalyst is ZSM-22 or ZSM-23.

31. The method of claim 30, wherein the zeolite oligomerization catalyst is a selectivated catalyst.

32. The method of claim 25, wherein the olefin feed contains less than 50 wt % alkane.

33. The method of claim 32, wherein the olefin feed contains at least 50 wt % olefin.

34. The method of claim 25, wherein the oxygenate is methanol or dimethyl ether.

35. The method of claim 25, wherein the hydrated olefin feed has a water content of 0.05 to 2 weight percent.

36. The method of claim 25, wherein the olefin feed stream comprises greater than 5 ppm by weight oxygenated hydrocarbon.

* * * * *